United States Patent
Staeuber et al.

(10) Patent No.: US 9,681,816 B2
(45) Date of Patent: Jun. 20, 2017

(54) DEVICE AND METHOD FOR LEAD FAILURE DETECTION

(71) Applicant: BIOTRONIK SE & Co. KG, Berlin (DE)

(72) Inventors: Philipp Staeuber, Berlin (DE); Andreas Neumann, Berlin (DE); Ulrich Busch, Berlin (DE); Peter Wohlgemuth, Chemnitz (DE); Sabrina Bauditz, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 14/594,288

(22) Filed: Jan. 12, 2015

(65) Prior Publication Data
US 2015/0224321 A1 Aug. 13, 2015

Related U.S. Application Data

(60) Provisional application No. 61/939,281, filed on Feb. 13, 2014.

(51) Int. Cl.
*A61B 5/02* (2006.01)
*A61B 5/0424* (2006.01)
*A61N 1/37* (2006.01)
*A61B 5/0452* (2006.01)
*A61N 1/05* (2006.01)
*A61N 1/08* (2006.01)

(52) U.S. Cl.
CPC .............. *A61B 5/0424* (2013.01); *A61N 1/37* (2013.01); *A61B 5/0452* (2013.01); *A61B 2560/0276* (2013.01); *A61N 1/056* (2013.01); *A61N 2001/083* (2013.01)

(58) Field of Classification Search
CPC ........ A61B 5/02; A61B 5/02133; A61N 1/37; A61N 1/365; A61N 1/36142
USPC .......................... 600/528, 508; 607/27, 5, 28
See application file for complete search history.

(56) References Cited

U.S. PATENT DOCUMENTS

| 4,630,204 A | * | 12/1986 | Mortara ............... | A61B 5/0464 128/901 |
| 8,712,523 B2 | * | 4/2014 | Sanghera ............. | A61N 1/0504 607/27 |
| 2011/0319782 A1 | * | 12/2011 | Sweeney ............ | A61B 5/02133 600/528 |

FOREIGN PATENT DOCUMENTS

| EP | 2476457 A1 | 7/2012 |
| WO | 2006076498 A2 | 7/2006 |
| WO | 2011072286 A1 | 6/2011 |

OTHER PUBLICATIONS

European Search Report received from EP Application Serial No. 15151619, dated Jul. 23, 2015, 4 pages.

* cited by examiner

*Primary Examiner* — Carl H Layno
*Assistant Examiner* — Jon Eric C Morales
(74) *Attorney, Agent, or Firm* — Arc IP Law, PC; Joseph J. Mayo

(57) ABSTRACT

A device and method that detects a lead failure condition for a lead having at least one electrode in contact with body tissue, wherein the lead is connected to the device. The device includes a first filter that filters an electric signal sensed by the at least one electrode to a first filtered signal, and a lead failure detection unit that detects signal characteristics of the first filtered signal. The lead failure detection (Continued)

unit indicates a lead failure condition when the detected signal characteristics correspond to a step response of the first filter.

10 Claims, 4 Drawing Sheets

DEVICE AND METHOD FOR LEAD FAILURE DETECTION

This application claims the benefit of U.S. Provisional Patent Application 61/939,281 filed on 13 Feb. 2014, the specification of which is hereby incorporated herein by reference.

BACKGROUND OF THE INVENTION

Field of the Invention

Embodiments of the invention generally relate to implantable medical devices, and, more particularly, implantable medical devices utilizing leads.

Description of the Related Art

Generally, implantable medical devices (IMD) for delivering a therapy or monitoring a physiologic condition of a human or animal body employ one or more elongated electrical leads in contact with the body tissue. Such IMD, typically, may monitor or deliver therapy to the heart, muscle, nerve, brain, and stomach or other organs. IMD such as pacemakers and implantable cardioverter defibrillators (ICD), for example, are typically used to treat cardiac arrhythmias by delivering electrical impulses to the heart. Such devices generally include sensing units that sense electrical cardiac activities through cardiac leads having one or more electrodes. When an abnormal rhythm is detected, typically, an appropriate electrical therapy is delivered by a therapy unit connected to cardiac leads.

Leads associated with such IMD typically include a lead body extending between a proximal lead end and a distal lead end. The lead body generally incorporates one or more exposed electrode or sensor elements located at or near the distal lead end. One or more elongated electrical conductors may typically extend through the lead body from a connector assembly provided at a proximal lead end for connection with an associated IMD and an electrode located at the distal lead end or along a section of the lead body. Each electrical conductor is typically electrically isolated from any other electrical conductors and is encased within an outer sheath that electrically insulates the lead conductors from body tissue and fluids.

Implantable medical leads typically extend from an implantation site of the IMD through an internal body pathway to a desired tissue site. The leads are generally small in diameter, highly flexible, and reliable lead bodies that withstand degradation by body fluids and body movements that apply stress and strain to the lead body and the connections made to electrodes. As lead bodies are made smaller and smaller and/or the number of lead conductors is increased, the integrity of lead conductors is generally increasingly important.

Implantable medical leads that extend to or in the heart (cardiac leads) are typically continuously flexed by the beating of the heart. Other stresses are generally applied to the lead body during an implantation or lead repositioning procedure, and by movements of the patient. For that reasons the lead may typically be slightly damaged, and the slight damage may progress until a lead conductor fractures and/or the insulation is breached causing an interruption of the electric conduction path or a short between conductors that are normally isolated. Also the connection of the lead to the IMD at the connector assembly may generally be interrupted or shortened. These effects may typically progress from an intermittent manifestation to a more continuous effect and may be referred to as "lead failures".

Lead failures typically adversely impact the normal operation of the IMD. Any interruption or short generally impedes sensing of electrical signals from the tissue and the stimulation of the tissue with electrical pulses. In the case of cardiac leads, generally, an interruption or a short may be misinterpreted by the IMD as intrinsic activity of the heart. This is generally known as oversensing or undersensing and may result in an incorrect interpretation of the cardiac data potentially resulting in inappropriate withholding or delivery of electrical therapy.

Generally, several methods have been developed to monitor lead integrity and detect lead failures. The most common method is the monitoring of lead impedance as significant changes of lead impedance are typically an indicator of lead failures. Impedance monitoring generally consumes energy and may interfere the sensing and is therefore not suited for continuous monitoring. In the case of discontinuous impedance monitoring, typically, intermittent lead failures may remain undetected.

Another method typically analyzes the intra cardiac electrogram (IEGM) waveform by comparing them with reference waveforms that represent physiological signals. This method generally requires the generation of reference waveforms. Due to the large variance of physiological waveforms, this method is typically susceptible for miss-detections.

In view of the above, there is a need for an improved method and device that detects lead failures.

BRIEF SUMMARY OF THE INVENTION

One or more embodiments of the invention provides a method and a device that detects lead failures based on an evaluation of detected interferenced electrical activity of the human or animal body.

At least one embodiment of the invention is based on the finding that lead failures, in particular intermittent lead failures, may cause a step response of the first filter in the processing chain of electrical signals detected by an electrode of the lead. This step response, in at least one embodiment, is different to physiological signals and may be easily detected in the signal after the first filter. Typically, any subsequent filtering before signal evaluation, as presented in common devices, changes the signal morphology such that the step response vanishes and the lead failure signal is more similar to physiological signals.

At least one embodiment of the invention includes a method to detect a lead failure condition for a lead having at least one electrode in contact with body tissue, wherein the method includes the steps of:

sensing an electric signal from the body tissue using the electrode, filtering the sensed electric signal using a first filter to a first filtered signal, detecting signal characteristics of the first filtered signal and indicating a lead failure condition if the detected signal characteristics correspond to the step response of the first filter.

In one or more embodiments, the first filter may be a high-pass filter. In at least one embodiment, the step of detecting signal characteristics may include one or more of the detection of an abrupt change of the signal amplitude and the detection of an exponential return of the signal amplitude to a previous mean signal amplitude. The abrupt change or step of the signal amplitude, in one or more embodiments, may be caused by a short or interrupt characteristic for a lead failure. In at least one embodiment, the exponential return of the signal amplitude to a previous mean signal amplitude is the characteristic step response of a high-pass filter. In one or more embodiments, the detection of an abrupt change of the signal amplitude may be performed by analyzing the slew rate of the signal amplitude. In at least one embodiment, the method may include the detection of a minimum slew rate of the signal amplitude. In one or more embodiments, the signal amplitude may be compared to one or more pre-determined thresholds or amplitude ranges at one or more pre-determined times or during pre-determined time windows. In at least one embodiment, an exponential return of the signal amplitude to a previous mean signal amplitude may be detected by comparing the signal amplitude to the determined step response of the first filter for the respective amplitude step. By way of at least one embodiment, as the return of the signal amplitude of a body signal to a previous mean signal amplitude is significantly shorter than the return in case of a step response, a simplified method to detect the exponential return may include the step of determination whether the time between the abrupt change of the signal amplitude and the return to a previous mean signal amplitude exceeds a predetermined time.

According to one or more embodiments, the method may include one or more additional steps of:
  filtering the first filtered signal using a second filter to a second filtered signal,
  detecting body signals in the second filtered signal, and
  marking detected body signals as invalid if a lead failure condition is indicated.

In at least one embodiment, the method may be applied to electric signals that are cardiac signals.

In one or more embodiments, the device may detect a lead failure condition for a lead having at least one electrode in contact with body tissue, wherein the lead is connected to the device. In at least one embodiment, the device may include at least a first filter to filter an electric signal sensed by the at least one electrode to a first filtered signal and a lead failure detection unit that is configured to detect signal characteristics of the first filtered signal. In one or more embodiments, a lead failure condition may be indicated by the lead failure detection unit if the detected signal characteristics correspond to the step response of the first filter.

In at least one embodiment of the invention, the first filter may be a high-pass filter. In one or more embodiments, the signal characteristics may include an abrupt change of the signal amplitude and an exponential return of the signal amplitude to a previous mean signal amplitude. In at least one embodiment, an abrupt change of the signal amplitude may be detected by analyzing the slew rate of the signal amplitude. In at least one embodiment, a minimum slew rate may be detected. In one or more embodiments, the signal amplitude may be compared to one or more predetermined thresholds or amplitude ranges at one or more pre-determined times or during pre-determined time windows. By way of at least one embodiment, an exponential return of the signal amplitude to a previous mean signal amplitude may be detected by comparing the signal amplitude to the determined step response of the first filter for the respective amplitude step. In one or more embodiments, a simplified method to detect the exponential return may include the determination of time between the abrupt change of the signal amplitude to a previous mean signal amplitude. In at least one embodiment of the invention, the device may further include a second filter to filter the first filtered signal to a second filtered signal, and a signal processing unit to detect body signals in the second filtered signal. In one or more embodiments, detected body signals may be marked as invalid if a lead failure condition is indicated by the lead failure detection unit when the detected signal characteristics correspond to the step response of the first filter.

In at least one embodiment of the invention, the electrode may be in contact with cardiac tissue. In one or more embodiments, the electrode may be part of a cardiac lead that is connected to an IMD such as a heart monitor or a heart stimulator, including pacemakers, implantable cardioverter defibrillators (ICD) or a device for cardiac resynchronization therapy (CRT) that detects cardiac signals.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
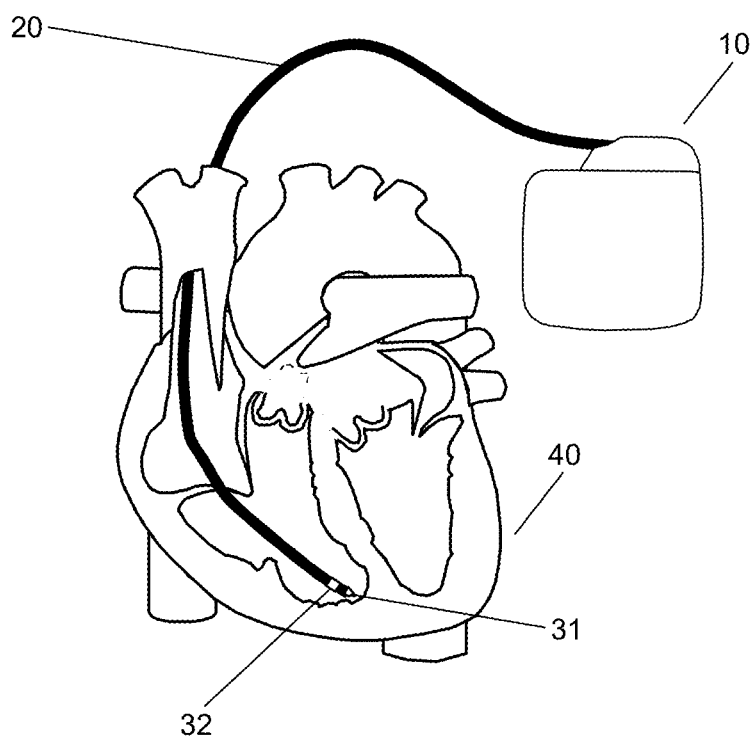
FIG. 1 is an illustration of a heart stimulation or heart monitoring system.

FIG. 1 shows a heart stimulation or heart monitoring system including an IMD 10, such as a heart stimulator or heart monitor, that is connected to a cardiac lead 20, according to one or more embodiments of the invention. In at least one embodiment, the distal end of the cardiac lead 20 may include one or more electrodes 31 and 32 that pick up electrical signals of the heart 40.

In one or more embodiments, sensing of electrical activity of the heart in the IMD 10 may be performed in different ways. As shown in FIG. 1, in at least one embodiment of the invention, electrical cardiac signals may be sensed between two electrodes 31 and 32 at the distal end of the cardiac lead 20, as bipolar sensing. In one or more embodiments, electrical cardiac signals may be sensed between one electrode 31 or 32 at the distal end of the cardiac lead 20 and the electrically conductive housing of the IMD 10, as unipolar sensing. In at least one embodiment of the invention, the IMD may be connected to multiple leads each having at least one electrode that extend to different tissue locations of the heart.

Figure 2:
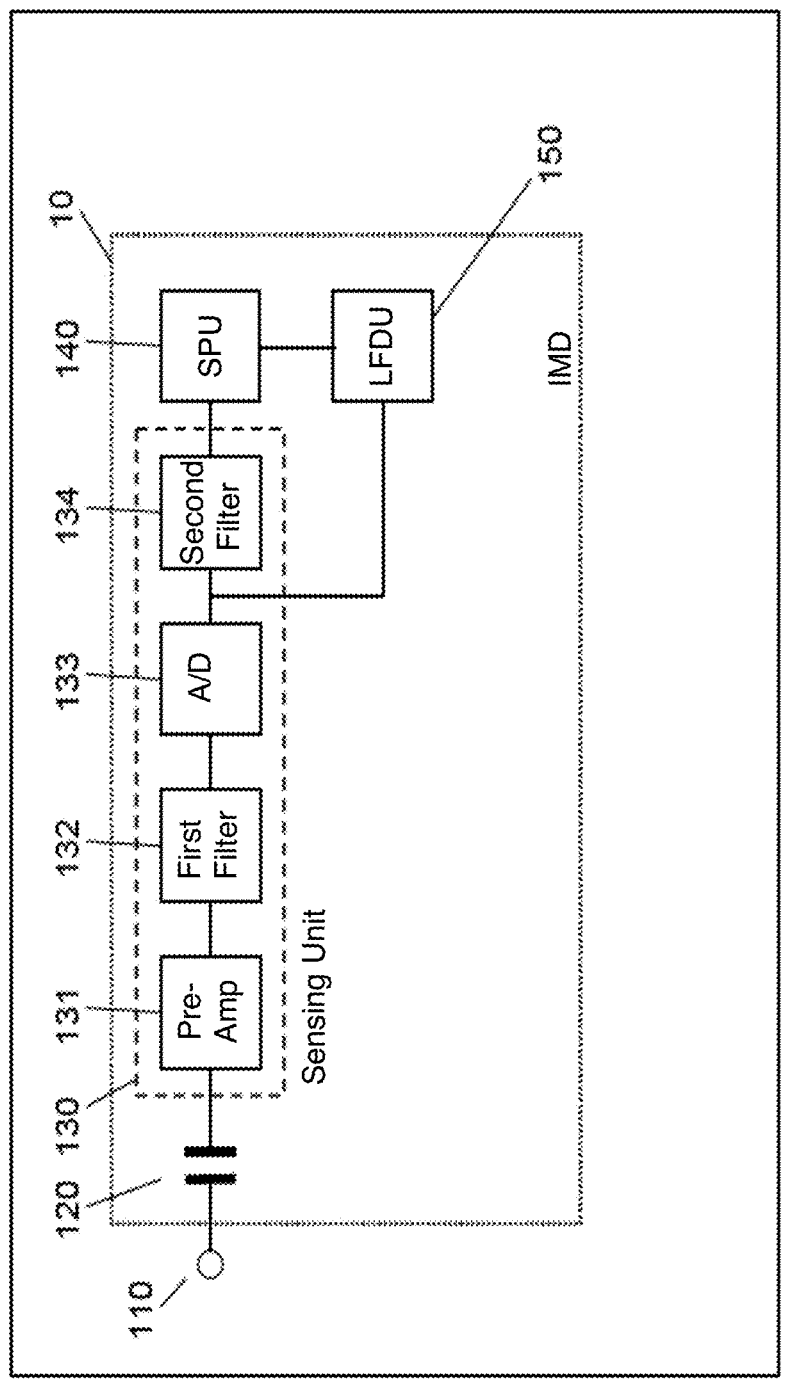
FIG. 2 is an illustration of an embodiment of an IMD.

FIG. 2 shows parts of the further structure of the IMD 10, according to one or more embodiments of the invention.

By way of at least one embodiment, the IMD 10 may include at least one electrode connection 110 that is coupled by a capacitor 120 to the input of a sensing unit 130 and optionally to the output of a stimulation unit (not illustrated in FIG. 2). In at least one embodiment, the capacitor 120 and input resistors of the sensing unit may form a first filter. In at least one embodiment, the first filter may be a high-pass filter. In one or more embodiments, the capacitor 120 may be replaced by an analogue filter. In at least one embodiment, the sensing unit 130 may output different signals to a signal processing unit 140 and to a lead failure detection unit 150, as will be described in detail hereafter. In one or more embodiments, a control unit (not illustrated in FIG. 2) may be connected to one or more of the sensing unit 130, the optional stimulation unit, the signal processing unit 140 and to the lead failure detection unit 150 to control their operation. In at least one embodiment, the control unit may include or may be connected to a memory to store one or more of operation parameters, operation commands and signals received from the other units of the IMD 10. In one or more embodiments, the signal processing unit 140 and the lead failure detection unit 150 may be in direct connection. In at least one embodiment, the cardiac stimulator may include a clock generator (not illustrated in FIG. 2), which provides clock signals.

According to one or more embodiments, the IMD 10 may include an electric energy source (not illustrated in FIG. 2), for example in the form of a battery or an accumulator, which supplies energy to the components of the IMD 10.

In at least one embodiment of the invention, the electric signal received by the electrode may run through capacitor 120 to an analogue pre-amplifier 131 and an optional analogue filter 132, and may then be converted using an A/D converter 133 into a digital signal. In at least one embodiment, the electric signal received by the electrode may first run through the analogue filter and may then be fed via the pre-amplifier to the A/D converter. In one or more embodiments, the analogue pre-amplifier 131 and the analogue filter 132 may be omitted. In at least one embodiment, the digital signal at the output of the A/D converter 133 may be a wideband filtered time-discrete and amplitude-discrete representation of the analogue input signal of the A/D converter 133 and may then be forwarded to the lead failure detection unit 150 and to a second filter 134. In one or more embodiments, the output signal of the second filter 134 may form a second filtered signal that is fed to a signal processing unit 140 to detect physiological events. For example, in at least one embodiment, electric signals from an electrode placed in the ventricle that are above a specific amplitude threshold value may be identified as natural contraction of the ventricle and are forwarded to the control unit. In one or more embodiments, the IMD may include one or more of multiple sensing units, processing units and lead detection units if multiple leads are connected, for example separate units for a right atrial lead and for a right ventricular lead.

By way of at least one embodiment, the lead failure detection unit 150 may receive the wideband filtered output signal of the A/D converter 133 and analyzes the signal to detect lead failures.

Figure 3:
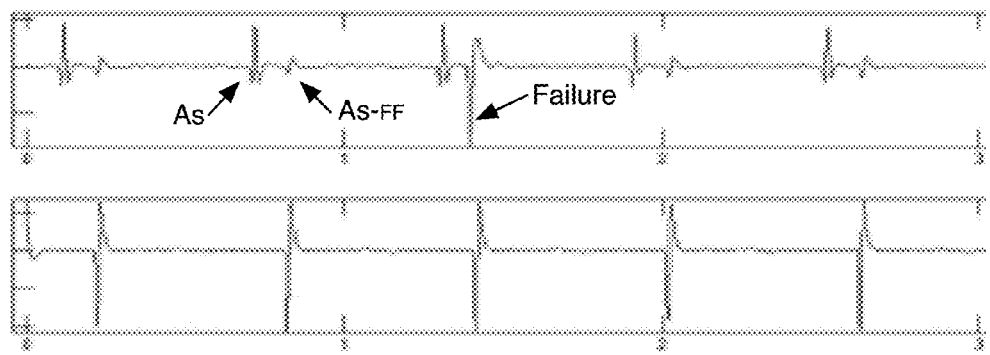
FIG. 3 is an illustration of atrial and ventricular electrocardiograms according to one embodiment of the invention.
Figure 4:
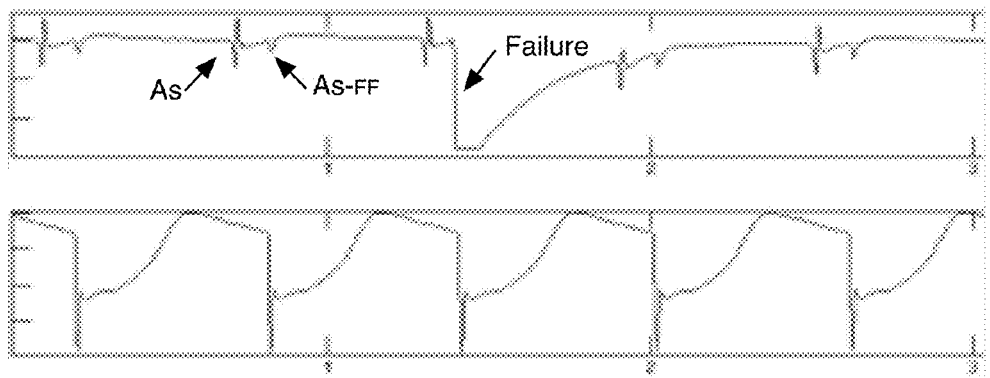
FIG. 4 is an illustration of atrial and ventricular electrocardiograms according to a further embodiment of the invention.

FIG. 3 shows a right atrial (upper trace) and a right ventricular (lower trace) electrocardiogram of atrial and ventricular signals over time during ventricular pacing at the output of the second filter 134, according to one or more embodiments of the invention. FIG. 4 shows the same right atrial (upper trace) and right ventricular (lower trace) electrocardiogram, but wideband filtered at the output of the A/D converter 133, according to one or more embodiments of the invention. In FIG. 3 and FIG. 4, by way of at least one embodiment, $A_S$ indicates a sensed atrial event and $A_{S\text{-}FF}$ indicates a far-field sensing of the ventricular depolarization. In one or more embodiments, failure indicates the point of time where the atrial electrode was in contact to the housing for a short time. In the filtered signal shown in FIG. 3, by way of at least one embodiment, the short appears as a peak similar to a sensed atrial event, having an amplitude significantly higher than the far field signal and may therefore be misinterpreted as sensed atrial event. FIG. 4 shows, according to one or more embodiments, that in the wideband filtered signal the short is represented by an abrupt drop of the atrial signal amplitude followed by an exponential return to the previous mean signal amplitude.

Figure 5:
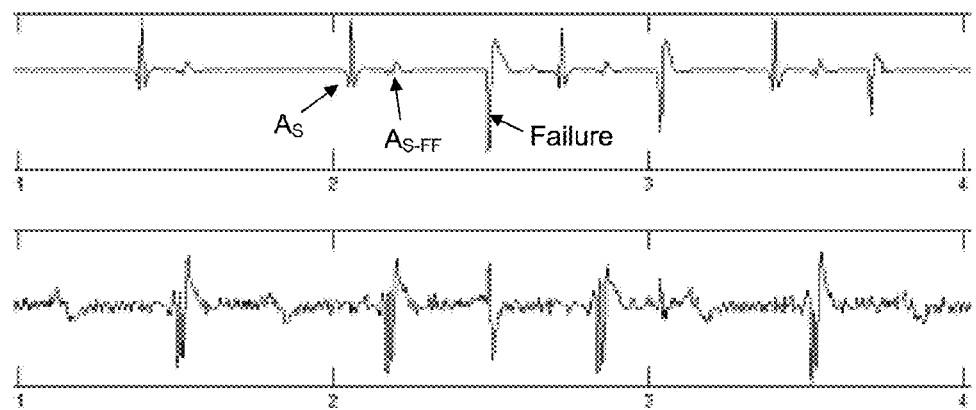
FIG. 5 is an illustration of atrial and ventricular electrocardiograms according to a further embodiment of the invention.
Figure 6:
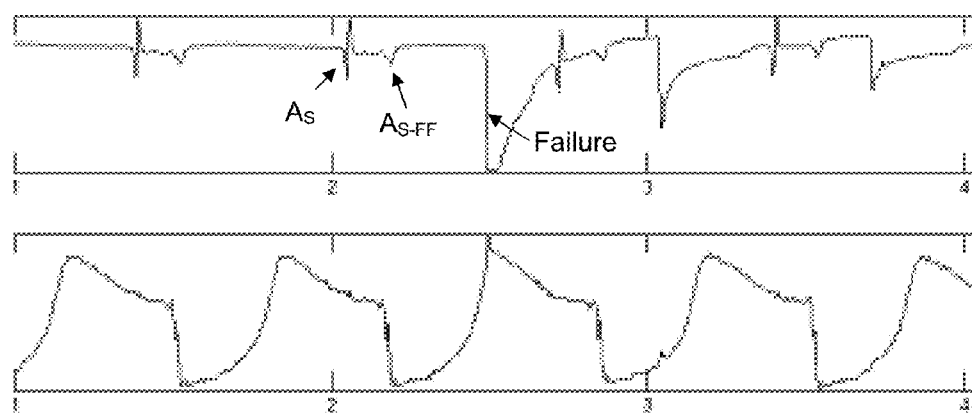
FIG. 6 is an illustration of atrial and ventricular electrocardiograms according to a further embodiment of the invention.

FIG. 5 shows a right atrial (upper trace) and a right ventricular (lower trace) electrocardiogram of atrial and ventricular signals over time without pacing at the output of the second filter 134, according to one or more embodiments of the invention. FIG. 6 shows the same right atrial (upper trace) and right ventricular (lower trace) electrocardiogram, but wideband filtered at the output of the A/D converter 133, according to one or more embodiments of the invention. In FIG. 5 and FIG. 6, in at least one embodiment, $A_S$ indicates a sensed atrial event and $A_{S\text{-}FF}$ indicates a far-field sensing of the ventricular intrinsic event. In one or more embodiments, failure indicates the point of time where the atrial electrode was in contact to another electrode for a short time. In the filtered signal shown in FIG. 5, by way of at least one embodiment, the short again appears as a peak similar to a sensed atrial event, having a amplitude significantly higher than the far field signal and may therefore be misinterpreted as sensed atrial event. FIG. 6 shows, according to one or more embodiments, that in the wideband filtered signal the short is represented by an abrupt drop of the atrial signal amplitude followed by an exponential return to the previous signal amplitude.

As shown in FIGS. 3, 4, 5 and 6, by way of at least one embodiment of the invention, lead failures may cause significant signal morphologies in the wideband filtered analog-digital converted signal. In one or more embodiments, lead failures such as shorts or interruptions, may cause impulses at the input connector 110. In at least one embodiment, the first filter formed by the capacitor 120 and input resistors may form a high-pass filter. In one or more embodiments, the step response may be detected at the output of the A/D converter 133. In at least one embodiment, the characteristic signal features of a lead failure condition may be an abrupt change of the signal amplitude followed by an exponential return to the previous mean signal amplitude.

In one or more embodiments, the lead failure detection unit 150 may continuously analyze the output signal of the A/D converter 133 for the occurrence of such characteristic signal features. In at least one embodiment, an abrupt change of the signal amplitude may be detected by analyzing the slew rate of the signal amplitude. In at least one embodiment, a minimum slew rate may be detected. In one or more embodiments, the signal amplitude may be compared to one or more predetermined thresholds or amplitude ranges at one or more pre-determined times or during pre-determined time windows. By way of at least one embodiment, the thresholds may be adaptive, for example a percentage of the mean or maximal or averaged signal amplitude. In at least one embodiment, the times or time-windows may also be adaptive, for example depending of the heart rate.

According to one or more embodiments, the return to the previous signal level may be slower than any intrinsic cardiac signal and may be detected by comparing the signal amplitude to the determined step response of the first filter for the respective amplitude step. In at least one embodiment of the invention, a simplified method to detect the exponential return may include the determination of time between the abrupt change of the signal amplitude and the return to a previous mean signal amplitude.

In one or more embodiments, if signal features characteristic for a lead failure condition are detected, lead failure detection unit 150 indicates a lead failure condition.

In at least one embodiment, signal processing unit (SPU) 140 may continuously analyze the output signal of filter 134 to detect body signals in the second filtered signal. In at least one embodiment, signal processing unit 140 may detect cardiac signals or cardiac events like P-waves, QRS-complexes or T-waves. If a body signal is detected and lead failure detection unit (LFDU) 150 indicates at the same time a failure condition, according to one or more embodiments, the detected body signal, such as the detected cardiac signals, may be marked as invalid. As such, in at least one embodiment, a wrong diagnosis or wrong therapy decision may be avoided.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A method to detect a lead failure condition for a lead having at least one electrode in contact with body tissue comprising:
    sensing an electric signal from the body tissue using said at least one electrode,
    filtering the sensed electric signal using a first filter to a first filtered signal by wideband filtering to enable low frequencies and high frequencies to pass through said first filter,
    detecting signal characteristics of the first filtered signal based on said low frequencies and said high frequencies,
    indicating a lead failure condition when said detected signal characteristics correspond to a step response of said first filter based on said low frequencies and said high frequencies wherein said detected signal characteristics comprise an exponential return of the amplitude to a previous mean signal amplitude,
    filtering the first filtered signal using a second filter to filter out the low frequencies to create a second filtered signal,
    detecting body signals in the second filtered signal, and,
    marking detected body signals as invalid when a lead failure condition is indicated.

2. The method of claim 1, wherein the second filter is a high-pass filter with a pre-defined low frequency cut-off value.

3. The method of claim 1, wherein the detection of an abrupt change of the amplitude comprises a step of detecting a minimum slew rate of the amplitude.

4. The method of claim 1, wherein said exponential return of the signal amplitude to a previous mean signal amplitude is detected when a time between the abrupt change of the amplitude and said exponential return exceeds a predetermined time.

5. The method of claim 1, wherein the electric signals are cardiac signals.

6. A device that detects a lead failure condition for a lead connected to the device and having at least one electrode in contact with body tissue, wherein the device comprises:
    a first filter that filters an electric signal sensed by the at least one electrode to a first filtered signal as a wideband filtered signal to enable low frequency signals and high frequency signals to pass through said first filter;
    a lead failure detection unit that detects signal characteristics of the first filtered signal as said low frequency signals and said high frequency signals;
    wherein a lead failure condition is indicated by the lead failure detection unit when said detected signal characteristics correspond to a step response of said first filter based on said low frequency signals and said high frequency signals wherein said detected signal characteristics comprise an exponential return of the amplitude to a previous mean signal amplitude;
    a second filter that filters the first filtered signal to filter out the low frequency signals to create a second filtered signal; and,
    a signal processing unit that detects body signals in the second filtered signal;
    wherein said detected body signals are marked as invalid when a lead failure condition is indicated.

7. The device of claim 6, wherein the second filter is a high-pass filter with a predefined low frequency cut-off value.

8. The device of claim 6, wherein said abrupt change of the amplitude is detected by detecting a minimum slew rate of the amplitude.

9. The device according to claim 6, wherein said exponential return of the amplitude to a previous mean signal amplitude is detected when a time between the abrupt change of the signal amplitude and said exponential return exceeds a predetermined time.

10. The device according to claim 6, wherein the electric signals are cardiac signals.

* * * * *